(12) United States Patent  (10) Patent No.: US 8,848,047 B2
Inuiya et al.  (45) Date of Patent: Sep. 30, 2014

(54) IMAGING DEVICE AND ENDOSCOPIC APPARATUS

(75) Inventors: Masafumi Inuiya, Ashigarakami-gun (JP); Yuichi Ohashi, Tokyo (JP); Mikio Ihama, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 1240 days.

(21) Appl. No.: 11/861,361

(22) Filed: Sep. 26, 2007

(65) Prior Publication Data

US 2008/0079806 A1    Apr. 3, 2008

(30) Foreign Application Priority Data

Sep. 28, 2006  (JP) ................................ 2006-264924
Sep. 28, 2006  (JP) ................................ 2006-264925

(51) Int. Cl.
 *A62B 1/04*    (2006.01)
 *H04N 3/14*    (2006.01)
 *H04N 5/33*    (2006.01)
 *H04N 9/04*    (2006.01)

(52) U.S. Cl.
 CPC ............... *H04N 9/045* (2013.01); *H04N 5/332* (2013.01)
 USPC .............. 348/65; 348/294; 348/273; 348/164

(58) Field of Classification Search
 USPC .................................. 348/65, 294, 273, 164
 See application file for complete search history.

(56) References Cited

U.S. PATENT DOCUMENTS

| 4,677,289 | A |   | 6/1987  | Nozaki et al. |              |
|-----------|---|---|---------|---------------|--------------|
| 4,886,721 | A |   | 12/1989 | Hayashida et al. |           |
| 5,453,611 | A | * | 9/1995  | Oozu et al.   | 250/208.1    |
| 5,512,940 | A | * | 4/1996  | Takasugi et al. | 348/71     |
| 5,739,851 | A | * | 4/1998  | Ohsawa et al. | 348/311      |
| 5,998,794 | A | * | 12/1999 | Spivey et al. | 250/370.09   |

(Continued)

FOREIGN PATENT DOCUMENTS

JP   61115355 A    6/1986
JP   63-186251 A   8/1988

(Continued)

OTHER PUBLICATIONS

English Abstract for JP1-280442, published Nov. 10, 1989 (also published as JP 2648494 which was filed in this application on Sep. 26, 2007), to Olympus Optical Co.

(Continued)

*Primary Examiner* — Viet Vu
*Assistant Examiner* — Herman Belcher
(74) *Attorney, Agent, or Firm* — Sughrue Mion, PLLC

(57) ABSTRACT

An imaging device comprising: in-substrate photoelectric converting devices arranged on the same plane in a semiconductor substrate; on-substrate photoelectric converting devices, formed on the same plane above the semiconductor substrate, each of which corresponds to each of at least a part of the in-substrate photoelectric converting devices and comprises a first electrode formed above the semiconductor substrate, a photoelectric converting layer formed on the first electrode and a second electrode formed on the photoelectric converting layer; a color filter layer that is formed above the semiconductor substrate and transmits a light in a different wave range from a wave range of a light to be absorbed by the photoelectric converting layer; and a signal reading section that reads a signal corresponding to an electric charge generated in the on-substrate photoelectric converting device and a signal corresponding to an electric charge generated in the in-substrate photoelectric converting device respectively.

16 Claims, 18 Drawing Sheets

(56) References Cited

U.S. PATENT DOCUMENTS

| | | | |
|---|---|---|---|
| 7,170,046 B2 * | 1/2007 | Higashitsutsumi | 250/226 |
| 2006/0119724 A1 * | 6/2006 | Inuiya | 348/311 |
| 2006/0169878 A1 * | 8/2006 | Kasano et al. | 250/226 |
| 2006/0186322 A1 * | 8/2006 | Matsuyama | 250/226 |
| 2007/0001094 A1 * | 1/2007 | Rhodes | 250/208.1 |
| 2007/0295389 A1 * | 12/2007 | Capps et al. | 136/251 |

FOREIGN PATENT DOCUMENTS

| | | |
|---|---|---|
| JP | 6-204445 A | 7/1994 |
| JP | 2002-217474 A | 8/2002 |
| JP | 2004-179266 A | 6/2004 |
| JP | 2004-179266 A | 8/2004 |
| JP | 20066922 A | 1/2006 |
| JP | 2006165663 A | 6/2006 |
| JP | 2006203457 A | 8/2006 |
| JP | 2006269922 A | 10/2006 |

OTHER PUBLICATIONS

Notification of Reasons for Refusal issued Sep. 6, 2011 by the Japanese Patent Office in counterpart Japanese Patent Application No. 2006264924.

Notification of Reasons for Refusal dated Dec. 6, 2011, issued by the Japanese Patent Office in counterpart Japanese Application No. 2006-264925.

Office Action dated Aug. 1, 2013, issued by the Korean Intellectual Property Office, in counterpart application No. 1020070098394, 9 pages in Korean and English.

* cited by examiner

- - - - - - : SPECTRAL SENSITIVITY OF PHOTOELECTRIC CONVERTING LAYER 9
———— : SPECTRAL TRANSMITTANCE OF PHOTOELECTRIC CONVERTING LAYER 9
· · · · · · · · · : PD

IMAGING DEVICE AND ENDOSCOPIC APPARATUS

CROSS-REFERENCE TO RELATED APPLICATIONS

This application is a new utility application claiming priority to JP 2006-264924 and JP 2006-264925, both filed Sep. 28, 2006, each incorporated herein by reference in its entirety.

BACKGROUND OF THE INVENTION

1. Field of the Invention

The present invention relates to an imaging device having a large number of photoelectric converting devices arranged on the same plane in a semiconductor substrate.

2. Description of the Related Art

An endoscopic apparatus including an image sensor of a CCD type or a CMOS type as an imaging device has already been used often on a medical site. The endoscopic apparatus is roughly divided into a frame sequential imaging method of using an imaging device capable of carrying out a monochromatic imaging to switch a filter for transmitting lights in wave ranges of R (red), G (green), B (blue) and IR (infrared) synchronously with a field frequency of the imaging device before a light source for illuminating an object through a fiber (for example, see Japanese Patent No. 2648494) and a simultaneous imaging method of picking up an image by using a single plate type imaging device mounting a color filter for transmitting the lights in the wave ranges of R, G and B with a white light set to be an illuminating light source.

The frame sequential imaging method serves to rotate a plurality of filters having different spectral transmittances before the light source and to pick up a plurality of images illuminated with lights having different wavelengths and to then synthesize a color image. For this reason, it is possible to obtain RGB color image data having information about three colors of RGB in one pixel data by using an RGB transmitting filter in a filter to be switched before the light source, for example. By sequentially switching an IR filter having two wavelengths which are apt to be absorbed into a hemoglobin in a blood and have bands narrowed, it is possible to obtain infrared image data causing one pixel data to have only information in an infrared region. According to an image based on the RGB color image data, it is possible to visually confirm an appearance of a portion to be an inspecting target. According to an image based on the infrared image data, it is possible to visually confirm information about a capillary vessel of a mucous membrane cortex and a mucous membrane fine pattern in the portion to be the inspecting target. In the frame sequential imaging, a color shift is generated for a moving object so that an image disturbance is caused.

On the other hand, the simultaneous imaging method serves to obtain the RGB color image data by an imaging and to then carry out an image processing over the RGB color image data, thereby generating infrared image data. According to the method, a color shift is not generated for a moving object. However, there is a problem in that precision in information of the infrared image data is low.

In the endoscopic apparatus, it is preferable that the RGB color image data causing one pixel data to have information about three colors of R, G and B and infrared image data causing one pixel data to have only information in an infrared region should be obtained by one imaging with high precision. However, there has not been proposed a method of obtaining the RGB color image data and the infrared image data by one imaging with high precision in the related art.

SUMMARY OF THE INVENTION

In consideration of the circumstances, it is an object of the invention to provide an imaging device capable of obtaining plural kinds of image data (for example, RGB color image data and infrared image data) by one imaging.

(1) An imaging device comprising: a semiconductor substrate; a plurality of in-substrate photoelectric converting devices arranged on the same plane in the semiconductor substrate; a plurality of on-substrate photoelectric converting devices, formed on the same plane above the semiconductor substrate, each of which corresponds to each of at least a part of said plurality of in-substrate photoelectric converting devices and comprises a first electrode formed above the semiconductor substrate, a photoelectric converting layer formed on the first electrode and a second electrode formed on the photoelectric converting layer; a color filter layer that is formed above the semiconductor substrate and transmits a light in a different wave range from a wave range of a light to be absorbed by the photoelectric converting layer; and a signal reading section that reads a signal corresponding to an electric charge generated in the on-substrate photoelectric converting device and a signal corresponding to an electric charge generated in the in-substrate photoelectric converting device respectively.

(2) The imaging device according to (1), wherein the color filter layer comprises a plurality of color filters corresponding to said plurality of in-substrate photoelectric converting devices respectively, and said plurality of color filter comprises plural types of color filters that transmit lights in different wave ranges from each other.

(3) The imaging device according to (2), wherein said plurality of color filters comprise three types of color filters that transmits lights in different wave ranges from each other.

(4) The imaging device according to (2), wherein said plurality of color filters comprise at least three types of color filters that transmit lights in different wave ranges from each other, said at least three types of color filters transmit a part of a light in a visible region respectively and at least one of said at least three types of color filters also transmits a light in an infrared region, and the photoelectric converting layer absorbs the light in the infrared region and generates an electric charge corresponding thereto, and transmits lights other than the light in the infrared region.

(5) The imaging device according to (4), wherein said plurality of color filters comprise a color filter that transmits a light in a wave range of R (red), a color filter that transmits a light in a wave range of G (green) and a color filter that transmits a light in a wave range of B (blue).

(6) The imaging device according to (5), wherein the color filter that transmits the light in the wave range of R also transmits the light in the infrared region, and the part of said plurality of in-substrate photoelectric converting devices correspond to the color filter that transmits the light in the wave range of R.

(7) The imaging device according to (4), wherein said plurality of color filters comprise a color filter that transmits a light in a wave range of Cy (cyan), a color filter that transmits a light in a wave range of G (green) or a light in a wave range of Mg (magenta) and a color filter that transmits a light in a wave range of Ye (yellow).

(8) The imaging device according to (2), wherein the color filter layer comprises a plurality of color filters corresponding to said plurality of in-substrate photoelectric converting devices respectively, said plurality of color filters comprise at least three types of color filters that transmit lights in different wave ranges from each other, one of said at least three types of color filters transmits a light in an infrared region and the others of said at least three types of color filters transmit a part of a light in a visible region respectively, and the photoelectric converting layer absorbs a light in a part of the visible region and generates an electric charge corresponding thereto, and transmits the other lights.

(9) The imaging device according to (8), wherein said plurality of color filters comprise a color filter that transmits a light in a wave range of Cy (cyan), a color filter that transmits the light in the infrared region, and a color filter that transmits a light in a wave range of Ye (yellow), and the photoelectric converting layer absorbs a light in a wave range of G (green).

(10) The imaging device according to (9), wherein the part of said plurality of in-substrate photoelectric converting devices correspond to the color filter that transmits the light in the wave range of Cy or the color filter that transmits the light in the wave range of Ye.

(11) The imaging device according to any of (1) to (10), wherein the color filter is formed above the on-substrate photoelectric converting device.

(12) The imaging device according to (11), further comprising a protective layer, provided between the on-substrate photoelectric converting device and the color filter layer, that protects the on-substrate photoelectric converting device formed by an atomic layer chemical vapor deposition method, wherein the photoelectric converting layer comprises an organic material.

(13) The imaging device according to (12), wherein the protective layer comprises an inorganic material.

(14) The imaging device according to (13), wherein the protective layer has a two-layer structure that comprises an inorganic layer including an inorganic material and an organic layer including an organic polymer.

(15) The imaging device according to any of (1) to (14), further comprising a microlens, provided above the color filter layer, that collects a light into each of said plurality of in-substrate photoelectric converting devices.

(16) An endoscopic apparatus comprising: the imaging device according to any of (1) to (15), and an image data generating section that generates image data corresponding to a time that an inspecting target is visually seen and image data obtained by causing an internal change in the inspecting target to be visible from a signal obtained by picking up an image through the imaging device.

DETAILED DESCRIPTION OF THE INVENTION

Embodiments according to the invention will be described below with reference to the drawings.

First Embodiment

Figure 1:
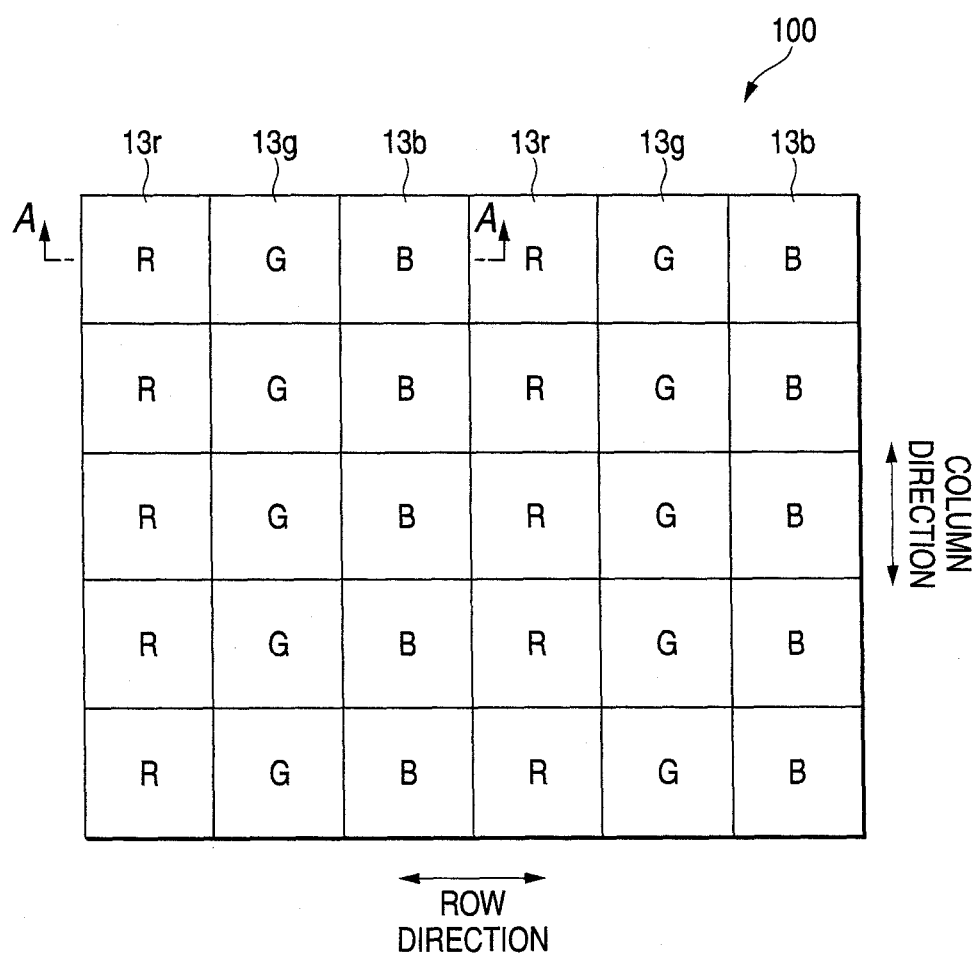
FIG. 1 is a typical view showing a partial surface of an imaging device for explaining embodiments according to the invention.
Figure 2:
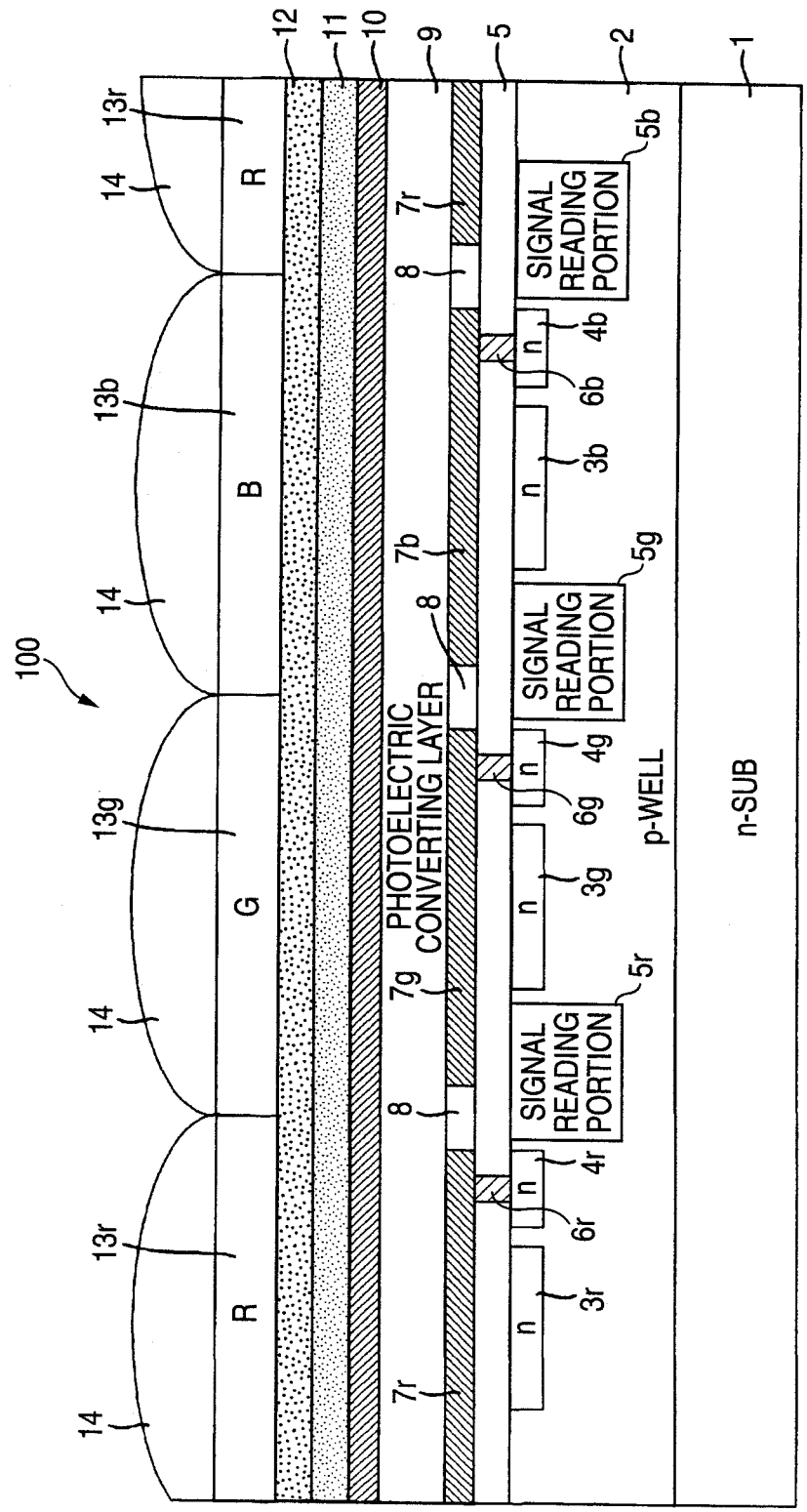
FIG. 2 is a typical sectional view showing the imaging device illustrated in FIG. 1 which is taken along an A-A line.

FIG. 1 is a typical view showing a partial surface of an imaging device for explaining the embodiments according to the invention. FIG. 2 is a typical sectional view showing the imaging device illustrated in FIG. 1 which is taken along an A-A line. In FIG. 1, a microlens 14 is not shown.

A p-well layer 2 is formed on an n-type silicon substrate 1. Both the n-type silicon substrate 1 and the p-well layer 2 will be hereinafter referred to as a semiconductor substrate. In a row direction on the same plane above the semiconductor substrate and a column direction which is orthogonal thereto, there are arranged large numbers of color filters of three types, that is, color filters 13r for mainly transmitting a light in a wave range of R, color filters 13g for mainly transmitting a light in a wave range of G and color filters 13b for mainly transmitting a light in a wave range of B, respectively.

A well-known material can be used for the color filter 13r. The material transmits a part of a light in an infrared region in addition to the light in the wave range of R. A well-known material can be used for the color filter 13g. The material transmits a part of the light in the infrared region in addition to the light in the wave range of G. A well-known material can be used for the color filter 13b. The material transmits a part of the light in the infrared region in addition to the light in the wave range of B.

For an array of the color filters 13r, 13g and 13b, it is possible to employ a color filter array (a Bayer array, a row stripe or a column stripe) used in a well-known single plate type solid state imaging device.

An n-type impurity region (hereinafter referred to as an n region) 3r is formed corresponding to the color filter 13r in the p-well layer 2 below the color filter 13r, and an R photoelectric converting device corresponding to the color filter 13r is constituted by a pn junction of the n region 3r and the p-well layer 2.

An n region 3g is formed corresponding to the color filter 13g in the p-well layer 2 below the color filter 13g, and a G photoelectric converting device corresponding to the color filter 13g is constituted by a pn junction of the n region 3g and the p-well layer 2.

An n region 3b is formed corresponding to the color filter 13b in the p-well layer 2 below the color filter 13b, and a B photoelectric converting device corresponding to the color filter 13b is constituted by a pn junction of the n region 3b and the p-well layer 2.

A transparent electrode 7r is formed above the n region 3r, a transparent electrode 7g is formed above the n region 3g and a transparent electrode 7b is formed above the n region 3b. The transparent electrodes 7r, 7g and 7b are divided corresponding to the color filters 13r, 13g and 13b, respectively. The transparent electrodes 7r, 7g and 7b are constituted by transparent materials to a visible light and an infrared light respectively, and ITO and IZO can be used, for example. The transparent electrodes 7r, 7g and 7b are buried in an insulating layer 8, respectively.

A photoelectric converting layer 9 having a one-sheet structure which mainly absorbs a light in an infrared region having a wavelength of 580 nm or more and generates an electric charge corresponding thereto, and transmits a light in a visible region (a wavelength of approximately 380 nm to 580 nm) other than the infrared region and is common to the color filters 13r, 13g and 13b is formed on each of the transparent electrodes 7r, 7g and 7b. For a material constituting the photoelectric converting layer 9, a phthalocyanine based organic material or a naphthalocyanine based organic material is used, for example.

A transparent electrode 10 having a one-sheet structure which is common to the respective color filters 13r, 13g and 13b is formed on the photoelectric converting layer 9. The transparent electrode 10 is constituted by a transparent material to a visible light and an infrared light, and ITO and IZO can be used, for example.

By the transparent electrode 7r, the transparent electrode 10 opposed thereto and a part of the photoelectric converting layer 9 interposed therebetween, a photoelectric converting device corresponding to the color filter 13r is formed. The photoelectric converting device will be hereinafter referred to as an R on-substrate photoelectric converting device because it is formed on the semiconductor substrate.

By the transparent electrode 7g, the transparent electrode 10 opposed thereto and a part of the photoelectric converting layer 9 interposed therebetween, a photoelectric converting device corresponding to the color filter 13g is formed. The photoelectric converting device will be hereinafter referred to as a G on-substrate photoelectric converting device.

By the transparent electrode 7b, the transparent electrode 10 opposed thereto and a part of the photoelectric converting layer 9 interposed therebetween, a photoelectric converting device corresponding to the color filter 13b is formed. The photoelectric converting device will be hereinafter referred to as a B on-substrate photoelectric converting device.

An n-type impurity region (hereinafter referred to as an n+ region) 4r having a high concentration for storing an electric charge generated in the photoelectric converting layer 9 of the R on-substrate photoelectric converting device is formed adjacently to the n region 3r in the p-well layer 2. In order to prevent a light from being incident on the n+ region 4r, it is preferable to provide a shielding film on the n+ region 4r.

An n+ region 4g for storing an electric charge generated in the photoelectric converting layer 9 of the G on-substrate photoelectric converting device is formed adjacently to then region 3g in the p-well layer 2. In order to prevent a light from being incident on the n+ region 4g, it is preferable to provide a shielding film on the n+ region 4g.

An n+ region 4b for storing an electric charge generated in the photoelectric converting layer 9 of the B on-substrate photoelectric converting device is formed adjacently to then region 3b in the p-well layer 2. In order to prevent a light from being incident on the n+ region 4b, it is preferable to provide a shielding film on the n+ region 4b.

A contact portion 6r formed of a metal such as aluminum is provided on the n+ region 4r and the transparent electrode 7r is formed on the contact portion 6r, and the n+ region 4r and the transparent electrode 7r are electrically connected to each other through the contact portion 6r. The contact portion 6r is buried in a transparent insulating layer 5 to a visible light and an infrared light.

A contact portion 6g formed of a metal such as aluminum is provided on the n+ region 4g and the transparent electrode 7g is formed on the contact portion 6g, and the n+ region 4g and the transparent electrode 7g are electrically connected to each other through the contact portion 6g. The contact portion 6g is buried in the insulating layer 5.

A contact portion 6b formed of a metal such as aluminum is provided on the n+ region 4b and the transparent electrode 7b is formed on the contact portion 6b, and the n+ region 4b and the transparent electrode 7b are electrically connected to each other through the contact portion 6b. The contact portion 6b is buried in the insulating layer 5.

A signal reading portion 5r for reading signals corresponding to electric charges generated in the R photoelectric converting device and stored in the n region 3r and the n+ region 4r respectively, a signal reading portion 5g for reading signals corresponding to electric charges generated in the G photoelectric converting device and stored in the n region 3g and the n+ region 4g respectively, and a signal reading portion 5b for reading signals corresponding to electric charges generated in the B photoelectric converting device and stored in the n region 3b and the n+ region 4b respectively are formed in regions other than the n regions 3r, 3g and 3b and the n+ regions 4r, 4g and 4b in the p-well layer 2. The signal reading portions 5r, 5g and 5b can employ a well-known structure using a CCD or an MOS circuit, respectively. In order to prevent a light from being incident on the signal reading portions 5r, 5g and 5b, it is preferable to provide a shielding film on the signal reading portions 5r, 5g and 5b.

Figure 3:
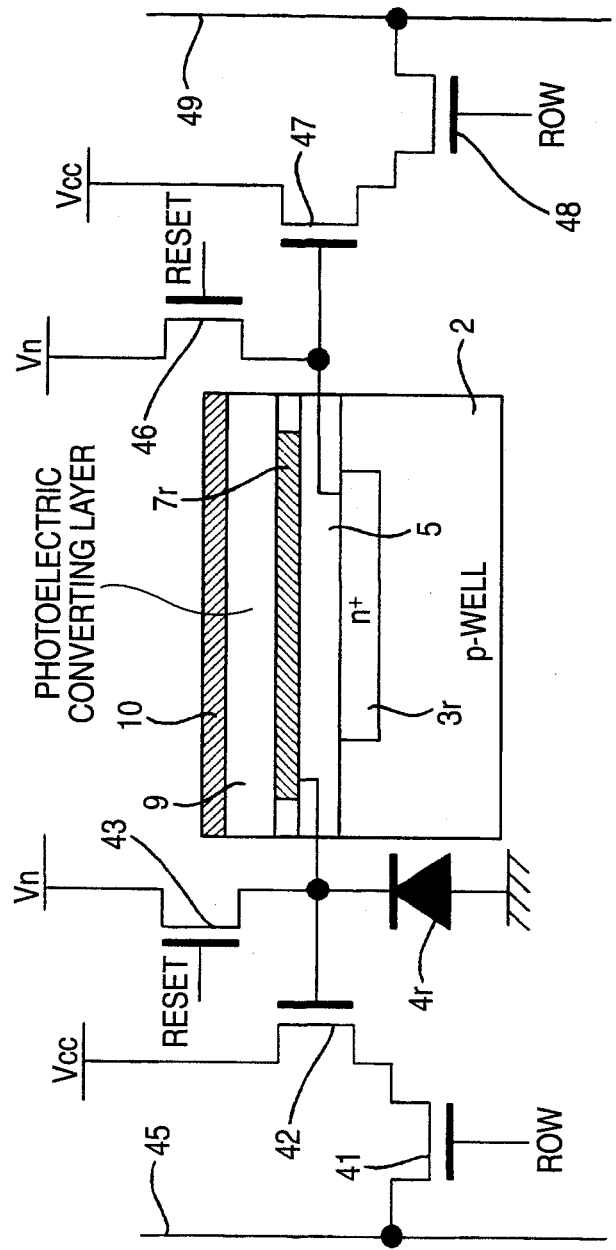
FIG. 3 is a diagram showing a specific example of a structure of a signal reading portion 5r illustrated in FIG. 2.

FIG. 3 is a diagram showing a specific example of a structure of the signal reading portion 5r illustrated in FIG. 2. In FIG. 3, the same structures as those in FIGS. 1 and 2 have the same reference numerals. Since the structures of the signal reading portions 5r, 5g and 5b are identical to each other, the description of the signal reading portions 5g and 5b will be omitted.

The signal reading portion 5r comprises a reset transistor 43 having a drain connected to the n+ region 4r and a source connected to a power supply Vn, an output transistor 42 having a gate connected to the drain of the reset transistor 43 and a source connected to a power supply Vcc, a row selecting transistor 41 having a source connected to a drain of the output transistor 42 and a drain connected to a signal output line 45, a reset transistor 46 having a drain connected to an n region 3r and a source connected to the power supply Vn, an output transistor 47 having a gate connected to the drain of the reset transistor 46 and a source connected to the power supply Vcc, and a row selecting transistor 48 having a source connected to a drain of the output transistor 47 and a drain connected to a signal output line 49.

When a bias voltage is applied between the transparent electrode 7r and the transparent electrode 10, an electric charge is generated corresponding to a light incident on the photoelectric converting layer 9 and is moved to the n+ region 4r through the transparent electrode 7r. The electric charge stored in the n+ region 4r is converted into a signal corresponding to an amount of the electric charge through the output transistor 42. When the row selecting transistor 41 is turned ON, a signal is output to the signal output line 45. After the signal is output, the electric charge in the n+ region 4r is reset by the reset transistor 43.

The electric charge generated in the R photoelectric converting device and stored in the n region 3r is converted into a signal corresponding to the amount of the electric charge by means of the output transistor 47. When the row selecting transistor 48 is turned ON, a signal is output to the signal output line 49. After the signal is output, the electric charge in the n region 3r is reset by the reset transistor 46.

Thus, the signal reading portion 5r can be constituted by a well-known MOS circuit including three transistors.

Returning to FIG. 2, protective layers 11 and 12 having a two-layer structure for protecting the on-substrate photoelectric converting device are formed on the photoelectric converting layer 9, and the color filters 13r, 13g and 13b are formed on the protective layer 12 and the microlens 14 for collecting a light into each of the n regions 3r, 3g and 3b corresponding to each of the color filters 13r, 13g and 13b is formed thereon.

An imaging device 100 is manufactured by forming the photoelectric converting layer 9 and then forming the color filters 13r, 13g and 13b and the microlens 14. However, the color filters 13r, 13g and 13b and the microlens 14 include a photolithographic step and a baking step. In the case in which an organic material is used as the photoelectric converting layer 9, therefore, the characteristic of the photoelectric converting layer 9 is deteriorated when the photolithographic step and the baking step are carried out in a state in which the photoelectric converting layer 9 is exposed. In the imaging device 100, the protective layers 11 and 12 are provided in order to prevent the characteristic of the photoelectric converting layer 9 from being deteriorated due to the manufacturing process.

It is preferable that the protective layer 11 should be an inorganic layer formed by an inorganic material through an atomic layer chemical vapor deposition method. The atomic layer chemical vapor deposition method is an atomic layer CVD method and can form a dense inorganic layer which can be an effective protective layer for the photoelectric converting layer 9. The atomic layer chemical vapor deposition method is also known as an ALE method or an ALD method. The inorganic layer formed by the atomic layer chemical vapor deposition method is preferably formed of $Al_2O_3$, $SiO_2$, $TiO_2$, $ZrO_2$, MgO, $HfO_2$ or $Ta_2O_5$ and is more preferably formed of $Al_2O_3$ or $SiO_2$, and is most preferably formed of $Al_2O_3$.

The protective layer 12 is formed on the protective layer 11 in order to enhance a protecting performance of the photoelectric converting layer 9 more greatly, and is preferably an organic layer formed of an organic polymer. For the organic polymer, parylene is preferable and parylene C is more preferable. The protective layer 12 may be omitted, and furthermore, the arrangement of the protective layers 11 and 12 may be inverted. By the structure shown in FIG. 2, the protecting effect of the photoelectric converting layer 9 is particularly high.

In the imaging device 100 having the structure described above, the light in the infrared region in any of the incident lights transmitted through the color filter 13r is absorbed into the photoelectric converting layer 9, and an electric charge corresponding to the light in the infrared region is generated therein. Similarly, the light in the infrared region in any of the incident lights transmitted through the color filter 13g is absorbed into the photoelectric converting layer 9, and an electric charge corresponding to the light in the infrared region is generated therein. Similarly, the light in the infrared region in any of the incident lights transmitted through the color filter 13b is absorbed into the photoelectric converting layer 9, and an electric charge corresponding to the light in the infrared region is generated therein.

When a predetermined bias voltage is applied to the transparent electrode 7r and the transparent electrode 10, the electric charge generated in the photoelectric converting layer 9 constituting the R on-substrate photoelectric converting device is moved to the n+ region 4r through the transparent electrode 7r and the contact portion 6r and is stored therein. A signal corresponding to the electric charge stored in the n+ region 4r is read by the signal reading portion 5r and is output to an outside of the imaging device 100.

When a predetermined bias voltage is applied to the transparent electrode 7g and the transparent electrode 10, similarly, the electric charge generated in the photoelectric converting layer 9 constituting the G on-substrate photoelectric converting device is moved to the n+ region 4g through the transparent electrode 7g and the contact portion 6g and is stored therein. A signal corresponding to the electric charge stored in the n+ region 4g is read by the signal reading portion 5g and is output to the outside of the imaging device 100.

When a predetermined bias voltage is applied to the transparent electrode 7b and the transparent electrode 10, similarly, the electric charge generated in the photoelectric converting layer 9 constituting the B on-substrate photoelectric converting device is moved to the n+ region 4b through the transparent electrode 7b and the contact portion 6b and is stored therein. A signal corresponding to the electric charge stored in the n+ region 4b is read by the signal reading portion 5b and is output to the outside of the imaging device 100.

Moreover, the light in the wave range of R which is transmitted through the color filter 13r and is then transmitted through the photoelectric converting layer 9 is incident on the R photoelectric converting device and the electric charge corresponding to the amount of the incident light is stored in the n region 3r. Similarly, the light in the wave range of G which is transmitted through the color filter 13g and is then transmitted through the photoelectric converting layer 9 is incident on the G photoelectric converting device and the electric charge corresponding to the amount of the incident light is stored in the n region 3g. Similarly, the light in the wave range of B which is transmitted through the color filter 13b and is then transmitted through the photoelectric converting layer 9 is incident on the B photoelectric converting device and the electric charge corresponding to the amount of the incident light is stored in the n region 3b. The electric charges stored in the n regions 3r, 3g and 3b are read by the signal reading portions 5r, 5g and 5b and are then output to the outside of the imaging device 100.

An array of the signals read and output from the n regions 3r, 3g and 3b is the same as the array of the signals output from the single plate type color solid state imaging device having the color filter array shown in FIG. 1. By carrying out a signal processing to be used in the single plate type color solid state imaging device, therefore, it is possible to generate color image data causing one pixel data to have data on three color components of R, G and B. Moreover, it is possible to generate infrared image data causing one pixel data to have data on an infrared color component by the signals read and output from the n+ regions 4r, 4g and 4b.

Thus, the imaging device 100 can output, to the outside, a signal having the R component corresponding to the electric charge generated in the R photoelectric converting device, a signal having the G component corresponding to the electric charge generated in the G photoelectric converting device, a signal having the B component corresponding to the electric charge generated in the B photoelectric converting device, a signal having an IR component corresponding to the electric charge generated in the R on-substrate photoelectric converting device, a signal having the IR component corresponding to the electric charge generated in the G on-substrate photoelectric converting device, and a signal having the IR component corresponding to the electric charge generated in the B on-substrate photoelectric converting device. By using the imaging device 100, therefore, it is possible to obtain two types of image data, that is, color image data and infrared image data by one imaging. Accordingly, the imaging device 100 can be utilized as an imaging device of an endoscopic apparatus requiring an appearance video of a portion to be an inspecting target of a human body and an internal video of the portion, for example.

Next, description will be given to the spectral sensitivity characteristic of the imaging device 100.

Figure 4:
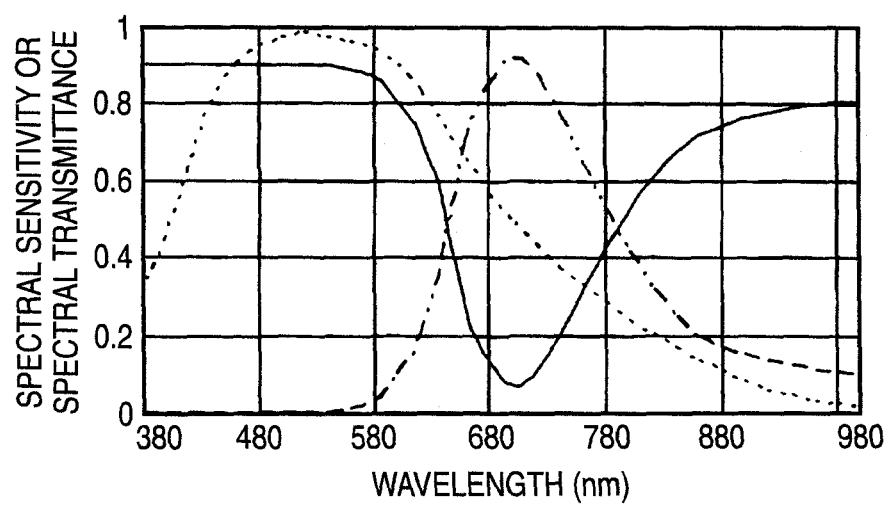
FIG. 4 is a chart showing characteristics of a photoelectric converting device and an on-substrate photoelectric converting device in the imaging device illustrated in FIG. 1.
Figure 5:
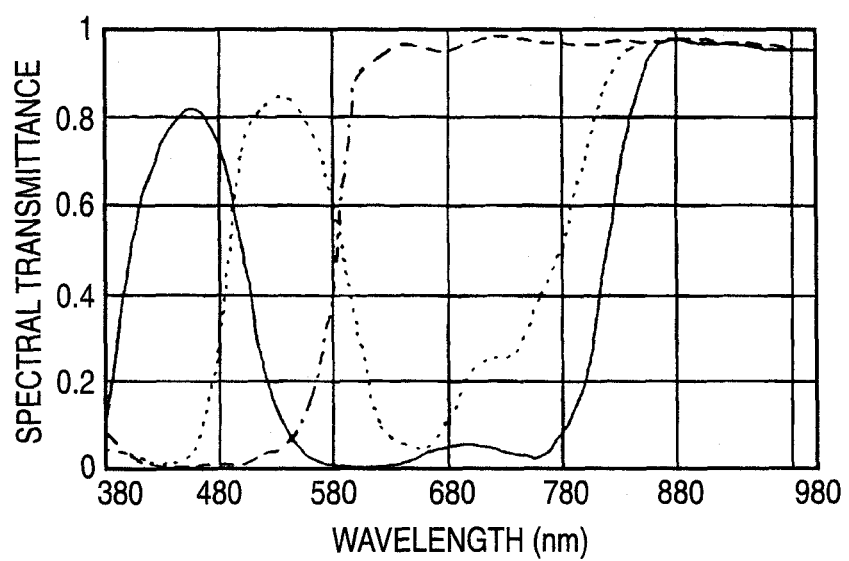
FIG. 5 is a chart showing a characteristic of a color filter of the imaging device illustrated in FIG. 1.

First of all, a spectral sensitivity characteristic of each photoelectric converting device (PD) formed in a semiconductor substrate is shown in FIG. 4, a spectral sensitivity characteristic of the photoelectric converting layer 9 is shown in FIG. 4, a spectral transmittance of the photoelectric converting layer 9 is shown in FIG. 4, and spectral transmittances of the color filters 13r, 13g and 13b are shown in FIG. 5. In FIG. 4, an axis of ordinates indicates a spectral sensitivity or a spectral transmittance obtained with one set to be a reference and an axis of abscissas indicates a wavelength of a light. In FIG. 5, an axis of ordinates indicates a spectral transmittance obtained with one set to be a reference and an axis of abscissas indicates a wavelength of a light.

Figure 6:
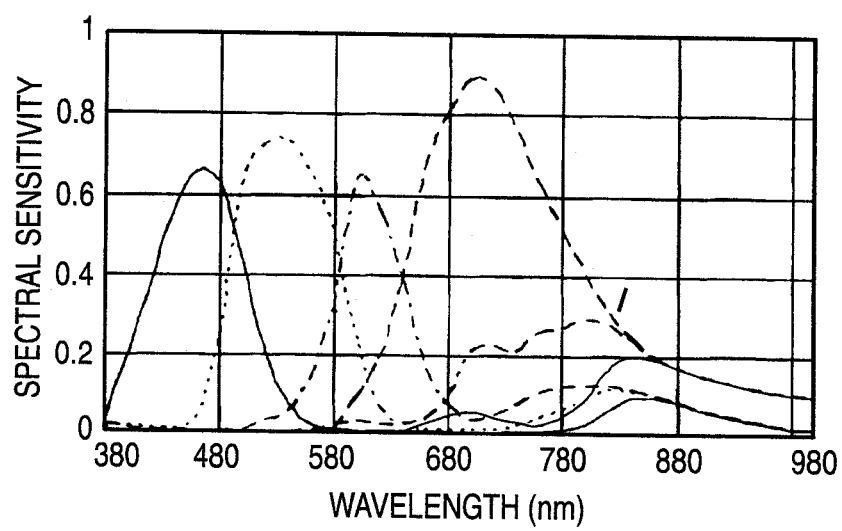
FIG. 6 is a chart showing a characteristic of the imaging device illustrated in FIG. 1 without a correcting filter.

When the characteristics are thus determined, a spectral sensitivity characteristic of the R photoelectric converting device is obtained as a product of the spectral transmittance of the photoelectric converting layer 9 and that of the color filter 13r, a spectral sensitivity characteristic of the G photoelectric converting device is obtained as a product of the spectral transmittance of the photoelectric converting layer 9 and that of the color filter 13g, and a spectral sensitivity characteristic of the B photoelectric converting device is obtained as a product of the spectral transmittance of the photoelectric converting layer 9 and that of the color filter 13b so that characteristics shown in FIG. 6 are obtained respectively. In FIG. 6, an axis of ordinates indicates a spectral sensitivity obtained with one set to be a reference and an axis of abscissas indicates a wavelength of a light.

Moreover, a spectral sensitivity characteristic of the R on-substrate photoelectric converting device is obtained as a product of the spectral sensitivity of the photoelectric converting layer 9 and the spectral transmittance of the color filter 13r, a spectral sensitivity characteristic of the G on-substrate photoelectric converting device is obtained as a product of the spectral sensitivity of the photoelectric converting layer 9 and the spectral transmittance of the color filter 13g, and a spectral sensitivity characteristic of the B on-substrate photoelectric converting device is obtained as a product of the spectral sensitivity of the photoelectric converting layer 9 and the spectral transmittance of the color filter 13b so that characteristics shown in FIG. 6 are obtained respectively.

Figure 7:
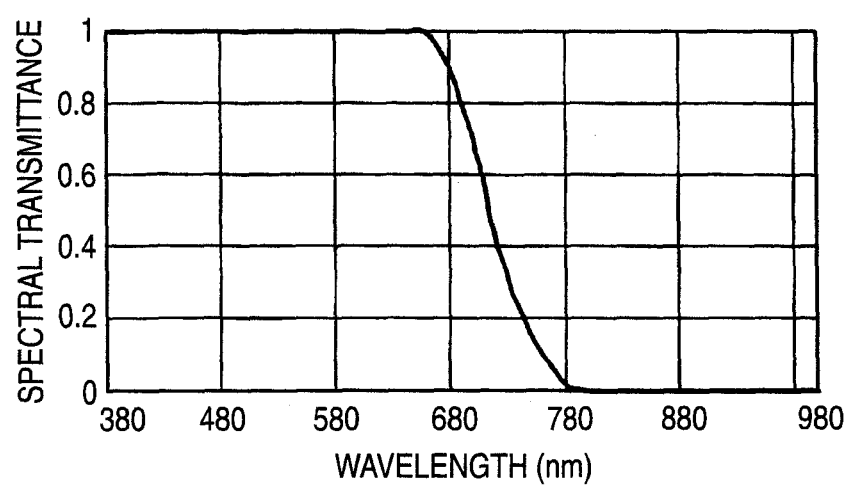
FIG. 7 is a chart showing a characteristic of the correcting filter.
Figure 8:
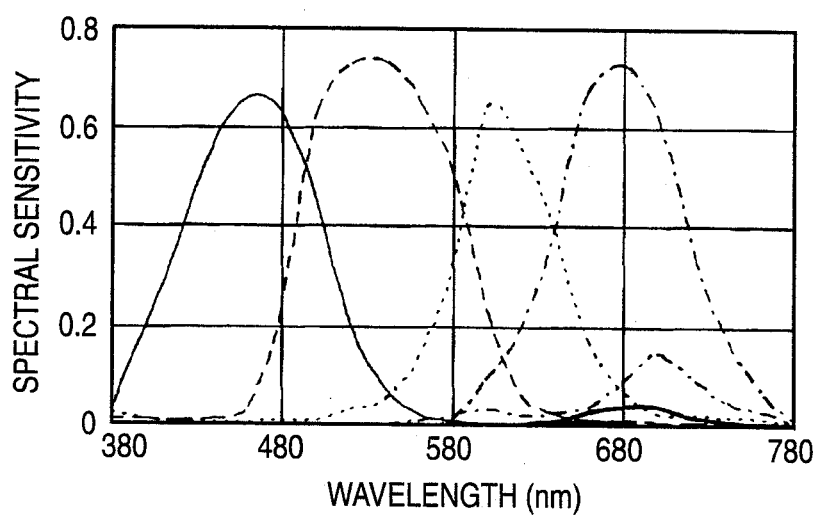
FIG. 8 is a chart showing a characteristic of the imaging device illustrated in FIG. 1 with the correcting filter.

When a correcting filter having a spectral transmittance shown in FIG. 7 is disposed on the light incident plane side of the imaging device 100 in order to regulate the spectral sensitivity characteristic of each on-substrate photoelectric converting device, the spectral sensitivity characteristic of the imaging device 100 shown in FIG. 8 is obtained. In FIG. 7, an axis of ordinates indicates a spectral transmittance obtained with one set to be a reference and an axis of abscissas indicates a wavelength of a light. In FIG. 8, an axis of ordinates indicates a spectral sensitivity obtained with one set to be a reference and an axis of abscissas indicates a wavelength of a light.

Figure 9:
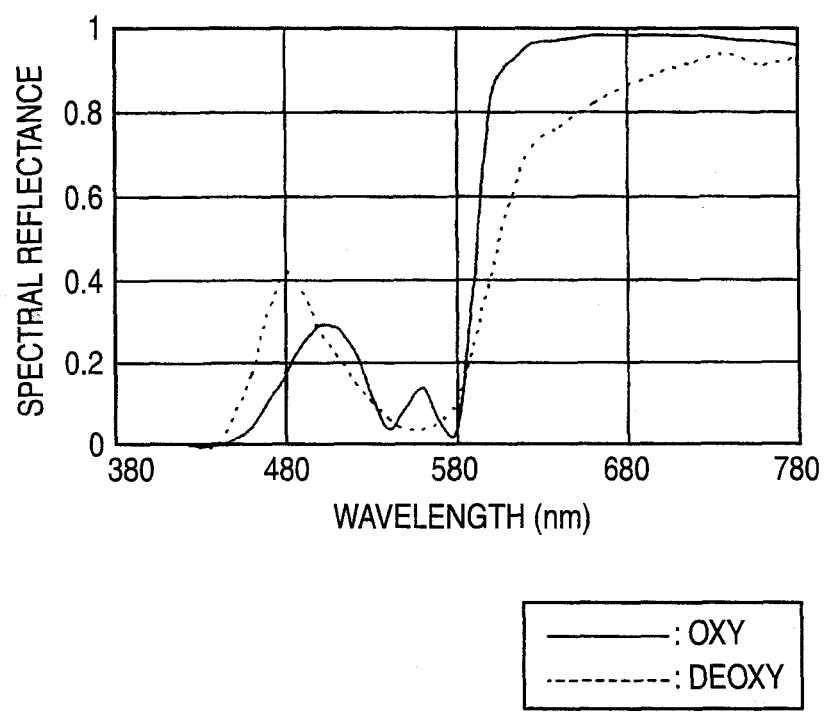
FIG. 9 is a chart showing a spectral reflectance of a hemoglobin.

FIG. 9 is a chart showing spectral reflectances of an oxygenated hemoglobin (oxy) and a reduced hemoglobin (deoxy). In FIG. 9, an axis of ordinates indicates a spectral reflectance obtained with one set to be a reference and an axis of abscissas indicates a wavelength of a light.

As is apparent from FIG. 9, the oxygenated hemoglobin and the reduced hemoglobin have a difference between both reflectances increased in a wave range having a wavelength of 580 nm to 780 nm. By using a photoelectric converting device having a sensitivity in the wave range, therefore, it is possible to represent a change in a state of the hemoglobin in an image with a high contrast. As shown in FIG. 8, in the image pickup device 100, the R on-substrate photoelectric converting device has a high sensitivity in the wave range of 580 nm to 780 nm. By using a signal obtained from the R on-substrate photoelectric converting device to generate infrared image data, therefore, it is possible to obtain, by one imaging, an appearance image having R, G and B colors in a portion to be an inspecting target and an image for knowing a change in a state of the hemoglobin in that portion.

In the case in which infrared image data are generated by using only the signal obtained from the R on-substrate photoelectric converting device, the signal obtained from the R on-substrate photoelectric converting device present around a position of a signal obtained from each of the G on-substrate photoelectric converting device and the B on-substrate photoelectric converting device may be used and interpolated in the same position to generate infrared image data having an equal resolution to that of color image data or only the signal obtained from the R on-substrate photoelectric converting device may be used to generate infrared image data having a resolution of ⅓ of the color image data. Alternatively, the signals obtained from three photoelectric converting devices, that is, the R on-substrate photoelectric converting device, the G on-substrate photoelectric converting device and the B on-substrate photoelectric converting device which are arranged in a row direction respectively may be added to obtain one signal, and the infrared image data having a resolution of ⅓ of the color image data may be generated based on the same signal.

By using the imaging device 100, it is possible to obtain two types of image data including color image data and infrared image data. The advantage can be obtained also in the case in which complementary colors as well as primary colors are used for the color filter to be utilized in the imaging device 100. Moreover, two types of image data cannot be obtained. By regulating a color scheme of the color filter of the imaging device 100 and a wave range of a light to be absorbed by the photoelectric converting layer, it is also possible to obtain RGB image data having a higher resolution than that of the single plate type imaging device. FIGS. 10A to 10D show an example of a structure of the imaging device 100 for obtaining the advantages. In FIGS. 10A to 10D, there are not shown components constituting the imaging device 100 other than the photoelectric converting device (PD) formed in the semiconductor substrate, the photoelectric converting layer formed above the PD and the color filter formed above the photoelectric converting layer.

Figure 10A:
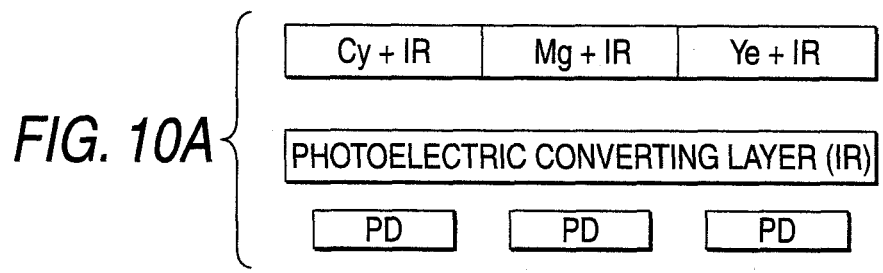
FIGS. 10A to 10D are diagrams showing a variant of a structure of the imaging device illustrated in FIG. 1.

An imaging device shown in FIG. 10A has such a structure that the color filter 13r is changed into a Cy filter for transmitting a light in a wave range of Cy (cyan) and a part of a light in an infrared light, the color filter 13g is changed into an Mg filter for transmitting a light in a wave range of Mg (magenta) and a part of the light in the infrared region, and the color filter 13b is changed into a Ye filter for transmitting a light in a wave range of Ye (yellow) and a part of the light in the infrared region in the imaging device 100 shown in FIGS. 1 and 2. For the Cy filter, the Mg filter and the Ye filter, it is preferable to use well-known materials respectively.

According to the structure, it is possible to generate color image data from signals of Cy, Mg and Ye obtained from the photoelectric converting device in the semiconductor substrate and to generate infrared image data from the signals obtained from the photoelectric converting layer. An array of the Cy filter, the Mg filter and the Ye filter is preferably set in such a manner that a color image can be reproduced.

Figure 10B:
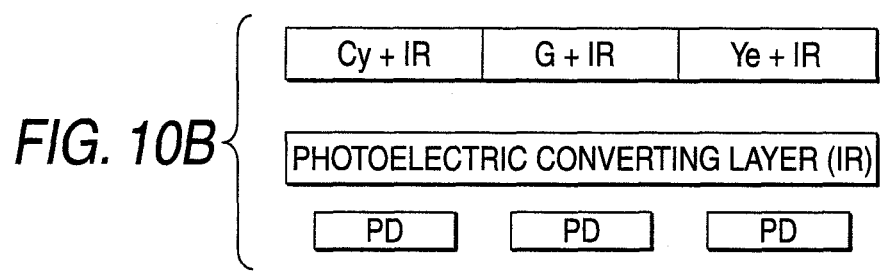

An imaging device shown in FIG. 10B has such a structure that the color filter 13r is changed into the Cy filter and the color filter 13b is changed into the Ye filter in the imaging device 100 shown in FIGS. 1 and 2.

According to the structure, it is possible to generate color image data from the signals of Cy, G and Ye obtained from the photoelectric converting devices in the semiconductor substrate and to generate infrared image data from the signals obtained from the photoelectric converting layer. The array of the Cy filter, the G filter and the Ye filter is preferably set in such a manner that a color image can be reproduced.

Figure 10C:
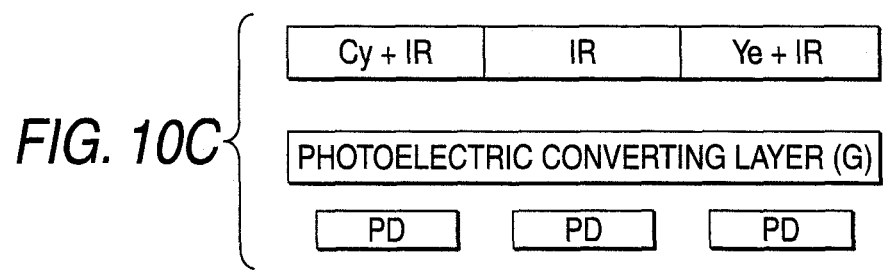

The imaging device shown in FIG. 10C has such a structure that the color filter 13r is changed into the Cy filter, the color filter 13g is changed into an IR filter for transmitting a light in an infrared region, the photoelectric converting layer 9 is changed into a G photoelectric converting layer for absorbing a light in a wave range of G and generating a signal charge corresponding thereto, and transmitting a light other than the wave range of G, and the color filter 13b is changed into the Ye filter in the imaging device 100 shown in FIGS. 1 and 2. For a material constituting the G photoelectric converting layer, it is possible to use InGaAlP or GaPAs, for example, in the case of an inorganic material and to use R6G/PMPS (rhodamine 6G (R6G)-doped polymethylphenylsilane), for example, in the case of an organic material.

According to the structure, color image data can be generated from signals of B and R which are obtained from the photoelectric converting device in the semiconductor substrate and a signal of G which is obtained from the photoelectric converting layer and infrared image data can be generated from an IR signal obtained from the photoelectric converting device provided below the IR filter. An array of the Cy filter and the Ye filter is preferably set in such a manner that a color image can be reproduced and an array of the IR filter is preferably set in such a manner that an infrared image can be reproduced.

Figure 10D:
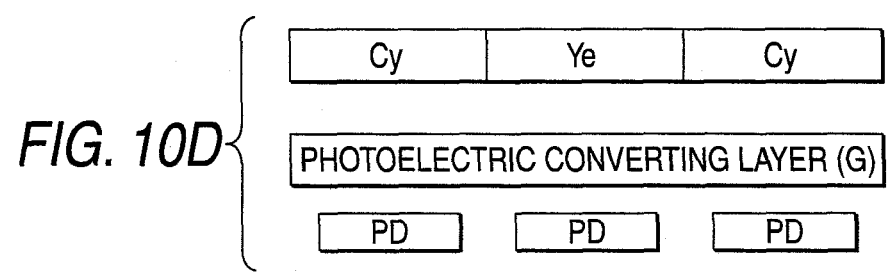

The imaging device shown in FIG. 10D has such a structure that the color filters 13r and 13b are changed into the Cy filters respectively, the color filter 13g is changed into the Ye filter, and the photoelectric converting layer 9 is changed into the G photoelectric converting layer in the imaging device 100 shown in FIGS. 1 and 2.

According to the structure, it is possible to generate color image data from the signals of B and R which are obtained from the photoelectric converting device in the semiconductor substrate and the signal of G which is obtained from the photoelectric converting layer. With the structure, a signal having two primary colors is obtained per imaging point. Therefore, it is possible to enhance a resolution more greatly than that in the single plate type imaging device.

The description has been given to the case in which two or three types of color filters are used for the imaging device 100. Even if four types of color filters or more are used, the same advantages can be obtained. Moreover, one type of color filter may be used. In this case, in the structure shown in FIG. 2, it is also possible to have a structure in which a G color filter having a one-sheet structure which serves to transmit a light in the wave range of G is provided in place of the color filters 13r, 13g and 13b, for example.

By the structure, it is possible to generate monochromatic image data in response to the signal obtained from the photoelectric converting device in the semiconductor substrate and to generate infrared image data in response to a signal obtained from the photoelectric converting layer 9. With the structure, moreover, there is also an advantage that the spectral sensitivity characteristic of the photoelectric converting layer can be regulated with the spectral transmittance of the color filter provided above the photoelectric converting layer.

While the photoelectric converting layer is provided above the semiconductor substrate and the color filter is provided thereabove in the description, it is possible to obtain the same advantages even if the arrangement of the photoelectric converting layer and the color filter is inverted.

While the color filters 13r, 13g and 13b also transmit the light in the infrared region respectively in the description, moreover, it is also possible to use a filter having such a spectral transmittance that the light in the infrared region cannot be transmitted. If any of the color filters does not transmit the light in the infrared region, the infrared image data cannot be generated. For this reason, at least one of one type of color filter or more is to have the function of transmitting the light in the infrared region.

While the three types of on-substrate photoelectric converting devices including the R on-substrate photoelectric converting device, the G on-substrate photoelectric converting device and the B on-substrate photoelectric converting device are provided in the description, moreover, it is sufficient that at least one of them is present in order to obtain infrared image data. As shown in FIGS. 6 and 8, the R on-substrate photoelectric converting device has the highest sensitivity in the infrared region. Therefore, it is the most preferable that the infrared image data should be generated by using the signal output from the R on-substrate photoelectric converting device. In the case in which the G on-substrate photoelectric converting device is omitted, it is preferable to omit the transparent electrode 7g, the contact portion 6g and the n+ region 4g in the structure shown in FIG. 2. In the case in which the B on-substrate photoelectric converting device is omitted, it is preferable to omit the transparent electrode 7b, the contact portion 6b and the n+ region 4b in the structure shown in FIG. 2.

In the case in which the structure shown in FIG. 10C is employed, moreover, it is possible to rarely obtain a signal having a G component from the on-substrate photoelectric converting device if only the on-substrate photoelectric converting device corresponding to the IR filter is provided in the imaging device. As a result, the generation of the color image data is hindered. For this reason, with the structure shown in FIG. 10C, it is necessary to provide at least the on-substrate photoelectric converting device corresponding to the Cy filter or the on-substrate photoelectric converting device corresponding to the Ye filter.

Next, description will be given to a method of manufacturing the imaging device 100. The imaging device 100 can be manufactured at the following steps (A) to (C).

(A) CMOS Substrate→Formation of Transparent Electrode

Form the n regions 3r, 3g and 3b and the signal reading portions on the silicon substrate in the same manner as in the related-art CMOS sensor.

Further form the n+ regions 4r, 4g and 4b and the signal reading portions.

Form the insulating layer 5 on the silicon substrate and form the transparent electrodes 7r, 7g and 7b thereon to cause the transparent electrodes 7r, 7g and 7b to come in contact with the n+ regions 4r, 4g and 4b by using a via plug.

Fill intervals among the transparent electrodes 7r, 7g and 7b with an insulating material and flatten the surfaces of the transparent electrodes 7r, 7g and 7b including the insulating material portion by using CMP.

The process is carried out in a semiconductor process.

(B) Formation of Photoelectric Converting Layer

Form the photoelectric converging layer 9 on the transparent electrodes 7r, 7g and 7b.

Further form the transparent electrode 10. The transparent electrode 10 is caused to come in contact with a pad which is not shown and a bias voltage is applied by an external power supply.

The process is carried out in a vacuum evaporation process.

(C) Formation of Microlens and Color Filter

Form an alumina protective layer on the photoelectric converting layer 9 by an atomic layer chemical vapor deposition method, for example, and further form a parylene C protective layer.

Subsequently form a mosaic color filter. Form the mosaic color filter in order of G resist application→pattern exposure→development→postbaking, B resist application→pattern exposure→development→postbaking, and R resist application→pattern exposure→development→postbaking.

Finally form the microlens. The microlens is formed in order of resist application→postbaking→resist application→pattern exposure→development→melt.

Second Embodiment

In the embodiment, description will be given to a configuration in which an imaging device 100 capable of obtaining the color image data and the infrared image data described in the first embodiment is applied to an endoscopic apparatus.

Figure 11:
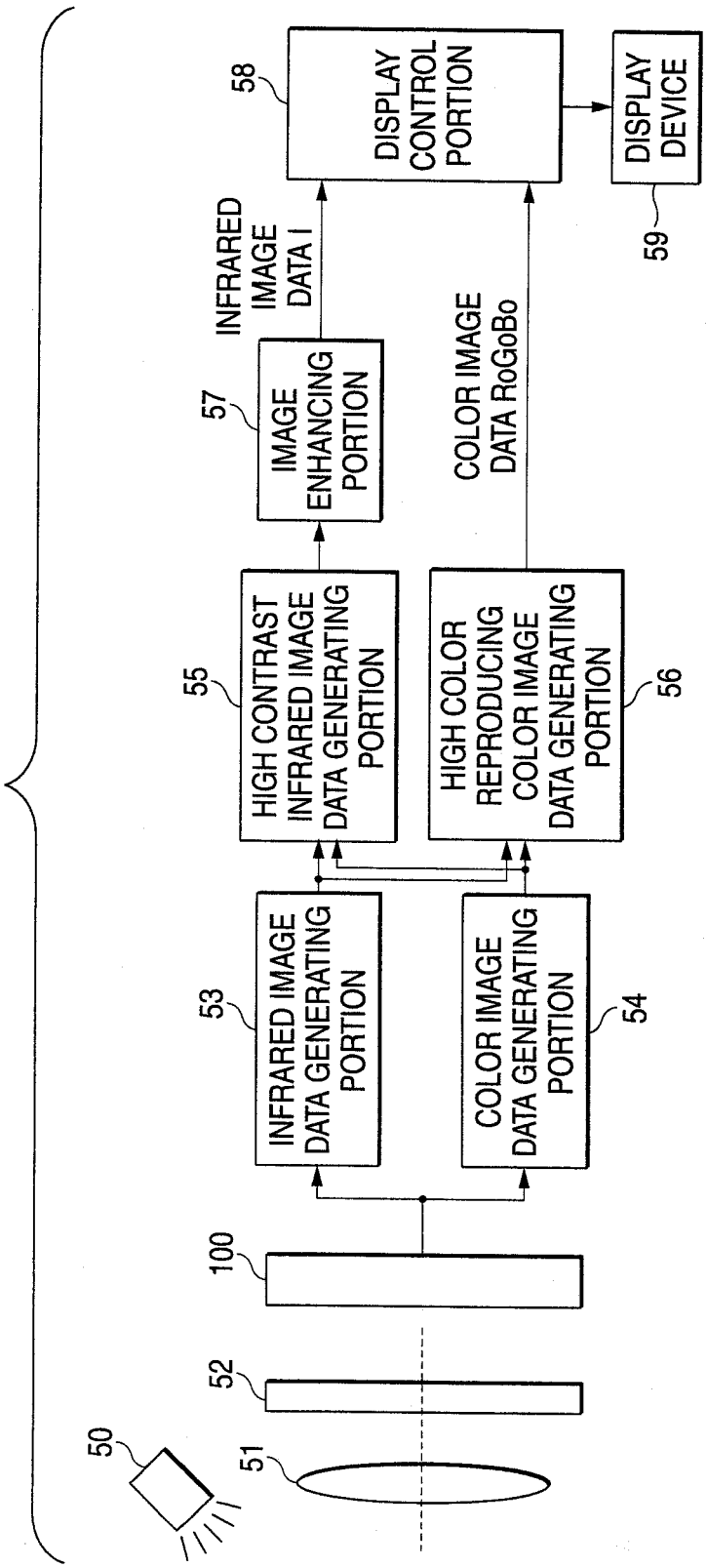
FIG. 11 is a diagram showing a schematic structure of an endoscopic apparatus for explaining a second embodiment.

FIG. 11 is a diagram showing a schematic structure of the endoscopic apparatus for explaining the second embodiment.

The endoscopic apparatus shown in FIG. 11 comprises a white light source 50 for illuminating a portion to be an inspecting target, an optical system 51 such as a photographing lens or a diaphragm, an imaging device 100 serving to receive a light passing through the optical system 51 and having the structure shown in FIGS. 1 and 2, a correcting filter 52 disposed between the imaging device 100 and the optical system 51 in order to correct a spectral sensitivity characteristic of a photoelectric converting layer 9 of the imaging device 100, an infrared image data generating portion 53 for generating infrared image data based on a signal corresponding to an electric charge generated in the photoelectric converting layer 9 of the imaging device 100, a color image data generating portion 54 for generating color image data based on a signal corresponding to an electric charge generated in each of an R photoelectric converting device, a G photoelectric converting device and a B photoelectric converting device in the imaging device 100, a high contrast infrared image data generating portion 55 for generating high contrast infrared image data having a contrast of the infrared image data generated in the infrared image data generating portion 53 enhanced by a calculation processing using the infrared image data generated in the infrared image data generating portion 53 and the color image data generated in the color image data generating portion 54, an image enhancing portion 57 for carrying out an enhancement processing over the high contrast infrared image data generated in the high contrast infrared image data generating portion 55, a high color reproducing color image data generating portion 56 for generating high color reproducing color image data having a color reproducibility of the color image data generated by the color image data generating portion 54 enhanced by a calculation processing using the infrared image data generated in the infrared image data generating portion 53 and the color image data generated in the color image data generating portion 54, and a display control portion 58 for carrying out such a control as to display, on a display device 59, an image based on the high contrast infrared image data obtained after the enhancement processing and an image based on the high color reproducing color image data.

It is sufficient that the imaging device 100 to be used in the endoscopic apparatus shown in FIG. 11 can output four types of signals, that is, a signal having an R component corresponding to a light in a wave range of R, a signal having a G component corresponding to a light in a wave range of G, a signal having a B component corresponding to a light in a wave range of B, and a signal having an IR component corresponding to a light in an infrared region, and the imaging device 100 is not restricted to the structure shown in FIGS. 1 and 2. For example, the imaging device 100 may be an imaging device having the structure shown in FIG. 10(c) or a single plate type imaging device in which four color filters, that is, a color filter for transmitting a light in a wave range of R or Cy, a color filter for transmitting a light in a wave range of G or Mg, a color filter for transmitting a light in a wave range of B or Ye, and a color filter for transmitting a light in an infrared region are arranged like a mosaic over the same plane above a semiconductor substrate. A spectral sensitivity characteristic of the imaging device 100 is shown in FIG. 8, for example.

The color image data generating portion 54 acquires, from the imaging device 100, the signal corresponding to the electric charge generated in the R photoelectric converting device of the imaging device 100 (which will be hereinafter referred to as an R signal), the signal corresponding to the electric charge generated in the G photoelectric converting device of the imaging device 100 (which will be hereinafter referred to as a G signal) and the signal corresponding to the electric charge generated in the B photoelectric converting device of the imaging device 100 (which will be hereinafter referred to as a B signal), and generates color image data by a well-known technique using these signals.

The infrared image data generating portion 53 carries out a single interpolation to generate infrared image data having an equal resolution to that of color image data from a signal corresponding to an electric charge generated in an R on-substrate photoelectric converting device of the imaging device 100 (which will be hereinafter referred to as an IRr signal).

Figure 12:
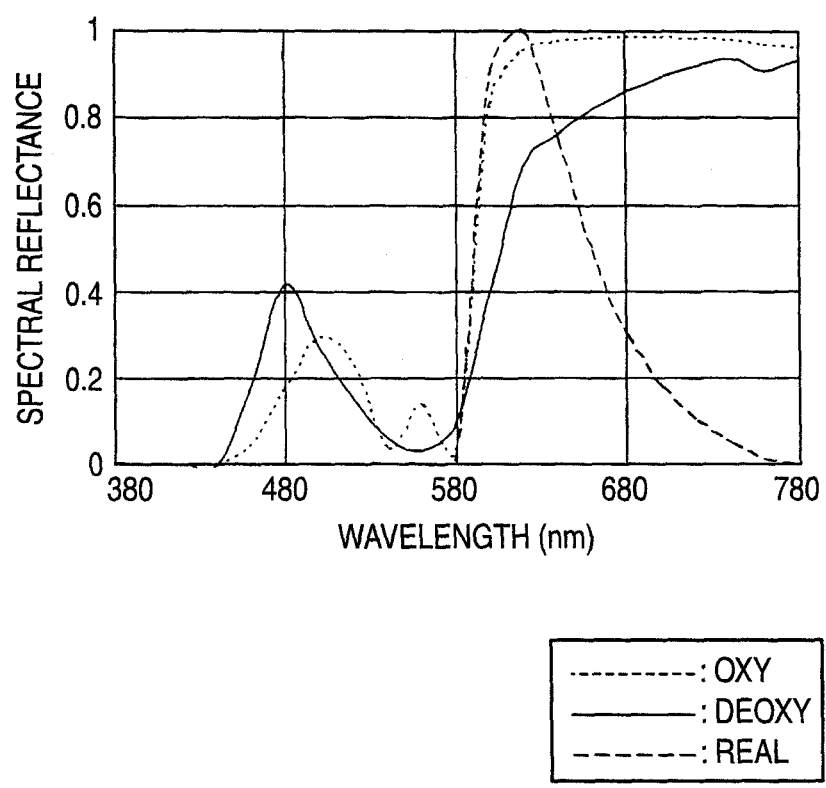
FIG. 12 is a chart showing a spectral sensitivity characteristic in which a spectral reflectance of a hemoglobin and a change in a state of the hemoglobin can be detected with the highest contrast.

FIG. 12 is a chart showing spectral reflectances of an oxygenated hemoglobin and a reduced hemoglobin. In FIG. 12, an axis of ordinates indicates a spectral reflectance obtained with one set to be a reference and an axis of abscissas indicates a wavelength of a light. In FIG. 12, when the axis of ordinates indicates a spectral sensitivity of a photoelectric converting device which is obtained with one set to be a reference, it is possible to detect a change in a state in the hemoglobin with the highest contrast by picking up an image of the hemoglobin by means of a photoelectric converting device having a spectral sensitivity shown in a Real curve of FIG. 12.

The high contrast infrared image data generating portion 55 can enhance the contrast of the infrared image data by carrying out such a calculation processing that the IRr signal obtained from the R on-substrate photoelectric converting device is close to a signal obtained from the photoelectric converting device having the spectral sensitivity characteristic shown in the Real curve of FIG. 12.

More specifically, the high contrast infrared image data generating portion 55 carries out a calculation shown in the following equation (1), thereby generating high contrast infrared image data.

$$I(x,y) = r1 \times R(x,y) + g1 \times G(x,y) + b1 \times B(x,y) + ir1 \times IR(x,y) \quad \text{Equation (1)}$$

I(x, y) represents pixel data in coordinates (x, y) of the high contrast infrared image data.

R(x, y) represents pixel data of an R component in coordinates (x, y) of color image data.

G(x, y) represents pixel data of a G component in the coordinates (x, y) of the color image data.

B(x, y) represents pixel data of a B component in the coordinates (x, y) of the color image data.

IR(x, y) represents pixel data of an IR component in coordinates (x, y) of infrared image data.

r1, g1, b1 and ir1 represent coefficients determined based on a spectral sensitivity characteristic of the R photoelectric converting device, a spectral sensitivity characteristic of the G photoelectric converting device, a spectral sensitivity characteristic of the B photoelectric converting device, a spectral sensitivity characteristic of the R on-substrate photoelectric converting device, and the spectral sensitivity characteristic expressed in the Real curve of FIG. 12.

The coefficients r1, g1, b1 and ir1 are determined by a method of least square in such a manner that Real (λ) approximates to a value obtained by a calculation of the following equation (2) most greatly when a spectral sensitivity in a wavelength λ of the R photoelectric converting device shown in FIG. 8 is represented by R(λ), a spectral sensitivity in the wavelength λ of the G photoelectric converting device shown in FIG. 8 is represented by G(λ), a spectral sensitivity in the wavelength λ of the B photoelectric converting device shown in FIG. 8 is represented by B(λ), a spectral sensitivity in the wavelength λ of the R on-substrate photoelectric converting device shown in FIG. 8 is represented by IR(λ), and a spectral sensitivity in the wavelength λ of the photoelectric converting device having the characteristic shown in the Real curve of FIG. 12 is represented by Real(λ). The determined coefficient data are prestored in a memory (not shown) in the endoscopic apparatus.

$$r1 \times R(\lambda) + g1 \times G(\lambda) + b1 \times B(\lambda) + ir1 \times IR(\lambda) \quad \text{Equation (2)}$$

Figure 13:
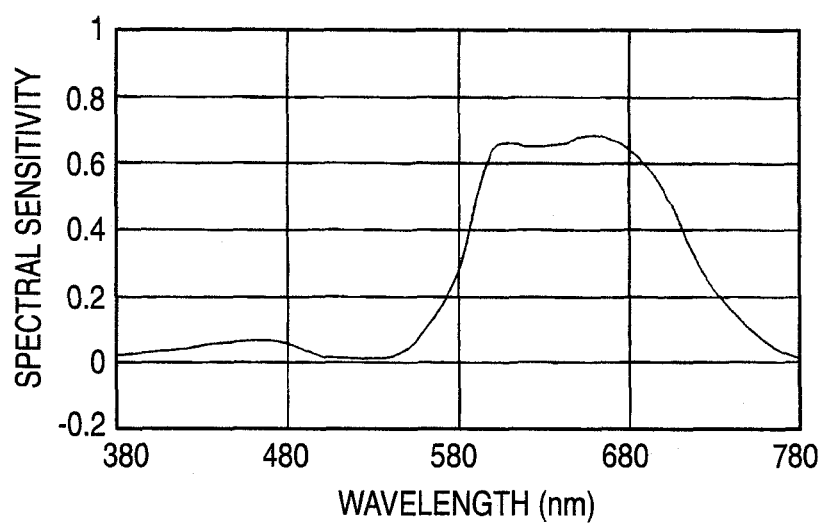
FIG. 13 is a chart showing a characteristic obtained by carrying out a processing of causing a characteristic of an R on-substrate photoelectric converting device of the imaging device illustrated in FIG. 1 to be close to the characteristic illustrated in a Real curve of FIG. 12.
Figure 13:
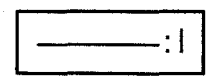

FIG. 13 is a chart showing a spectral sensitivity characteristic obtained as a result of a calculation of the Equation (2) by using the coefficients determined by the method. In FIG. 13, an axis of ordinates indicates a spectral sensitivity obtained with one set to be a reference and an axis of abscissas indicates a wavelength of a light. A curve I shown in FIG. 13 indicates a spectral sensitivity characteristic of a virtual photoelectric converting device which can acquire the high contrast infrared image data obtained by the calculation of the Equation (1).

Figure 14:
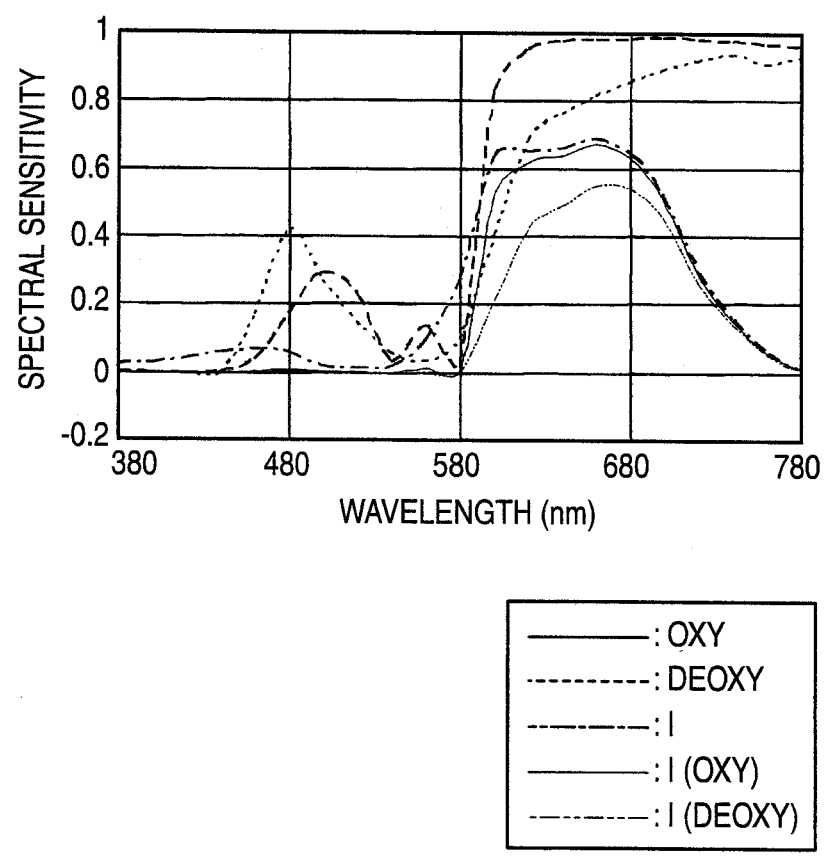
FIG. 14 is a chart showing a detecting sensitivity characteristic of a hemoglobin which is obtained when an image is picked up by the imaging device having the characteristic illustrated in FIG. 13.
Figure 15:
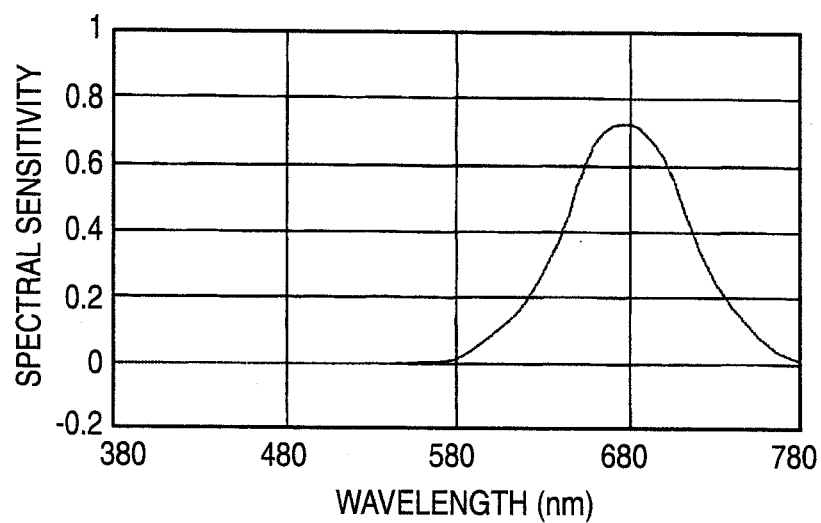
FIG. 15 is a chart showing a spectral sensitivity characteristic of the R on-substrate photoelectric converting device illustrated in FIG. 8.
Figure 16:
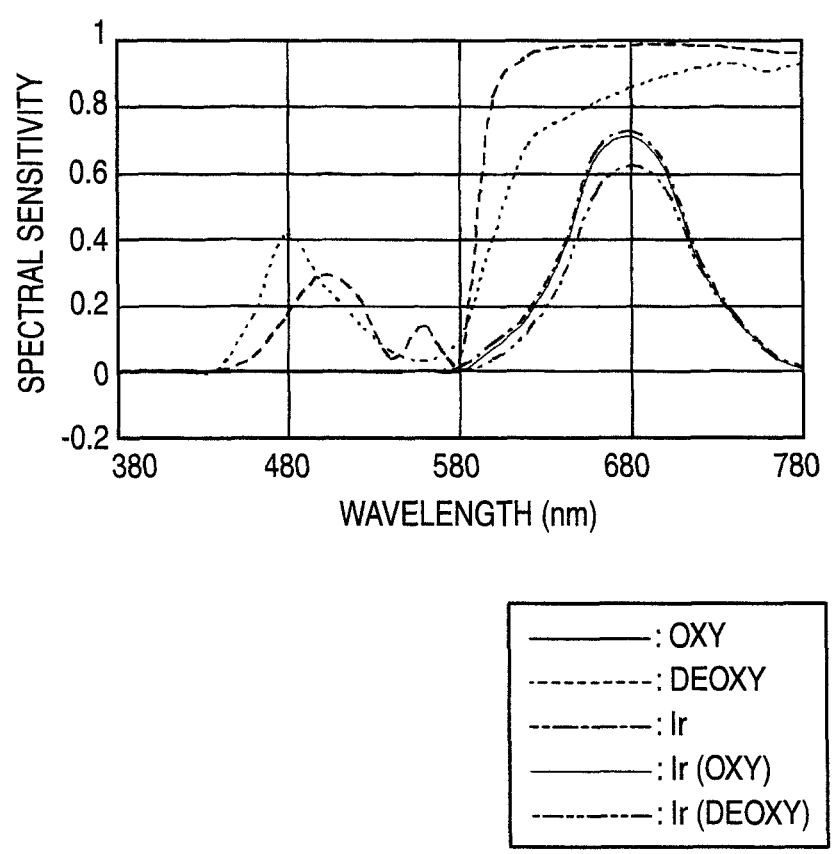
FIG. 16 is a chart showing a detecting sensitivity characteristic of the hemoglobin which is obtained when an image is picked up by an imaging device having the characteristic illustrated in FIG. 15.

FIG. 14 is a chart showing detection sensitivities of the oxygenated hemoglobin and the reduced hemoglobin in the case in which a light transmitted from the hemoglobin is detected by a photoelectric converting device having the spectral sensitivity characteristic shown in FIG. 13. In FIG. 14, an axis of ordinates indicates a spectral sensitivity obtained with one set to be a reference and an axis of abscissas indicates a wavelength of a light. FIG. 15 is a chart showing a spectral sensitivity characteristic of the R on-substrate photoelectric converting device illustrated in FIG. 8. In FIG. 15, an axis of ordinates indicates a spectral sensitivity obtained with one set to be a reference and an axis of abscissas indicates a wavelength of a light. FIG. 16 is a chart showing detection sensitivities of the oxygenated hemoglobin and the reduced hemoglobin in the case in which the light transmitted from the hemoglobin is detected by the R on-substrate photoelectric converting device having the spectral sensitivity characteristic illustrated in FIG. 15. In FIG. 16, an axis of ordinates indicates a spectral sensitivity obtained with one set to be a reference and an axis of abscissas indicates a wavelength of a light.

By a comparison between FIGS. 14 and 16, it is apparent that a contrast ratio of high contrast infrared image data which is expressed in a value obtained by dividing an area A surrounded by a waveform I(oxy) of the oxygenated hemoglobin and a straight line of a spectral sensitivity=0 shown in FIG. 14 by an area B surrounded by a waveform I(deoxy) of the reduced hemoglobin and the straight line of a spectral sensitivity=0 shown in FIG. 14 is 1.318, a contrast ratio of infrared image data which is expressed in a value obtained by dividing an area C surrounded by a waveform Ir(oxy) of the oxygenated hemoglobin and a straight line of a spectral sensitivity=0 shown in FIG. 16 by an area D surrounded by a waveform Ir(deoxy) of the reduced hemoglobin and the straight line of a spectral sensitivity=0 shown in FIG. 16 is 1.166, and the contrast of the infrared image data can be enhanced by an execution of the calculation processing shown in the Equation (1).

The imaging device to be used in the endoscopic apparatus according to the embodiment is to output an IR signal. For this reason, such an infrared cut filter as to be provided in an ordinary digital camera cannot be disposed on a front surface of the imaging device. In the embodiment, the correcting filter 52 for correcting the spectral sensitivity characteristic of the photoelectric converting layer 9 is provided. Although each of the R photoelectric converting device, the G photoelectric converting device and the B photoelectric converting device rarely has a sensitivity in a light in an infrared region, therefore, it has a slight sensitivity. As a result, there is a possibility that a color reproducibility of the color image data might be deteriorated.

Figure 17:
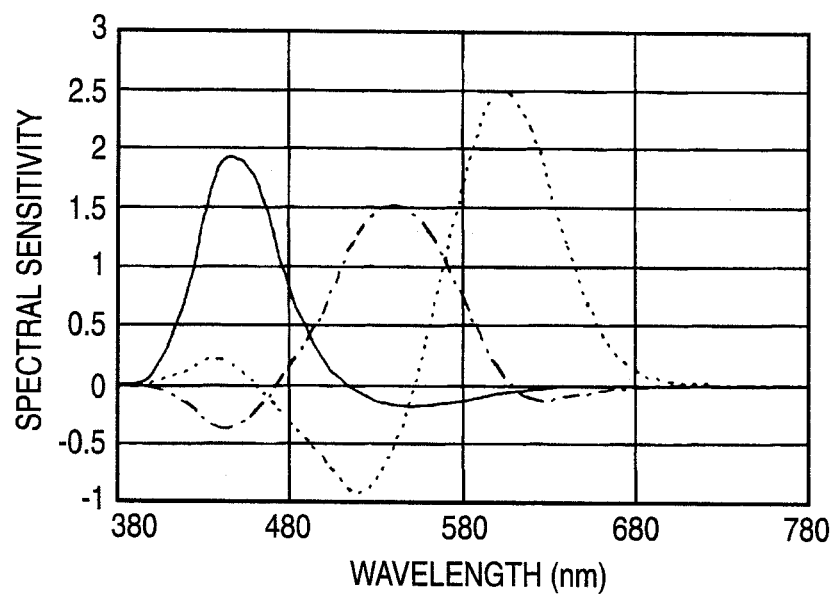
FIG. 17 is a chart showing a standard RGB ideal imaging characteristic.

The high color reproducing color image data generating portion 56 can generate the high color reproducing color image data by carrying out such a calculation processing that the R signal obtained from the R photoelectric converting device is close to a signal obtained from an r photoelectric converting device having an ideal spectral sensitivity characteristic defined by a standard RGB ideal imaging characteristic shown in FIG. 17, such a calculation processing that the G signal obtained from the G photoelectric converting device is close to a signal obtained from a g photoelectric converting device having the ideal spectral sensitivity characteristic defined by the standard RGB ideal imaging characteristic shown in FIG. 17, and such a calculation processing that the B signal obtained from the B photoelectric converting device is close to a signal obtained by a b photoelectric converting device having the ideal spectral sensitivity characteristic defined by the standard RGB ideal imaging characteristic shown in FIG. 17.

More specifically, the high color reproducing color image data generating portion 56 carries out a calculation shown in the following Equation (3), thereby enhancing a color reproducibility of the color image data.

$$\begin{pmatrix} Ro(x,y) \\ Go(x,y) \\ Bo(x,y) \end{pmatrix} = \begin{pmatrix} r2 & g2 & b2 & ir2 \\ r3 & g3 & b3 & ir3 \\ r4 & g4 & b4 & ir4 \end{pmatrix} \cdot \begin{pmatrix} R(x,y) \\ G(x,y) \\ B(x,y) \\ Ir(x,y) \end{pmatrix} \qquad \text{Equation (3)}$$

Ro(x, y) represents pixel data of an R component in coordinates (x, y) of high color reproducing color image data.

Go(x, y) represents pixel data of a G component in the coordinates (x, y) of the high color reproducing color image data.

Bo(x, y) represents pixel data of a B component in the coordinates (x, y) of the high color reproducing color image data.

R(x, y) represents pixel data of the R component in coordinates (x, y) of color image data.

G(x, y) represents pixel data of the G component in the coordinates (x, y) of the color image data.

B(x, y) represents pixel data of the B component in the coordinates (x, y) of the color image data.

Ir(x, y) represents pixel data of an IR component in coordinates (x, y) of infrared image data.

r2, r3, r4, g2, g3, g4, b2, b3, b4, ir2, ir3 and ir4 represent coefficients determined by the spectral sensitivity characteristic of the R photoelectric converting device, the spectral sensitivity characteristic of the G photoelectric converting device, the spectral sensitivity characteristic of the B photoelectric converting device, the spectral sensitivity characteristic of the R on-substrate photoelectric converting device, and the standard RGB ideal imaging characteristic shown in FIG. 17.

The coefficients r2, g2, b2 and ir2 are determined by the method of least square in such a manner that r(λ) approximates to a value obtained by the following equation (4) most greatly when the spectral sensitivity in the wavelength λ of the R photoelectric converting device shown in FIG. 8 is represented by R(λ), the spectral sensitivity in the wavelength λ of the G photoelectric converting device shown in FIG. 8 is represented by G(λ), the spectral sensitivity in the wavelength λ of the B photoelectric converting device shown in FIG. 8 is represented by B(λ), the spectral sensitivity in the wavelength λ of the R on-substrate photoelectric converting device shown in FIG. 8 is represented by IR(λ), and a spectral sensitivity in the wavelength λ of the r photoelectric converting device shown in FIG. 17 is represented by r(λ). The determined coefficient data are prestored in a memory (not shown) in the endoscopic apparatus.

$$r2 \times R(\lambda) + g2 \times G(\lambda) + b2 \times B(\lambda) + ir2 \times IR(\lambda) \qquad \text{Equation (4)}$$

The coefficients r3, g3, b3 and ir3 are determined by the method of least square in such a manner that g(λ) approximates to a value obtained by the following equation (5) most greatly when the spectral sensitivity in the wavelength λ of the g photoelectric converting device shown in FIG. 17 is represented by g(λ). The determined coefficient data are prestored in a memory (not shown) in the endoscopic apparatus.

$$r3 \times R(\lambda) + g3 \times G(\lambda) + b3 \times B(\lambda) + ir3 \times IR(\lambda) \qquad \text{Equation (5)}$$

The coefficients r4, g4, b4 and ir4 are determined by the method of least square in such a manner that b(λ) approximates to a value obtained by the following equation (6) most greatly when the spectral sensitivity in the wavelength λ of the b photoelectric converting device shown in FIG. 17 is represented by b(λ). The determined coefficient data are prestored in a memory (not shown) in the endoscopic apparatus.

$$r4 \times R(\lambda) + g4 \times G(\lambda) + b4 \times B(\lambda) + ir4 \times IR(\lambda) \qquad \text{Equation (6)}$$

Figure 18:
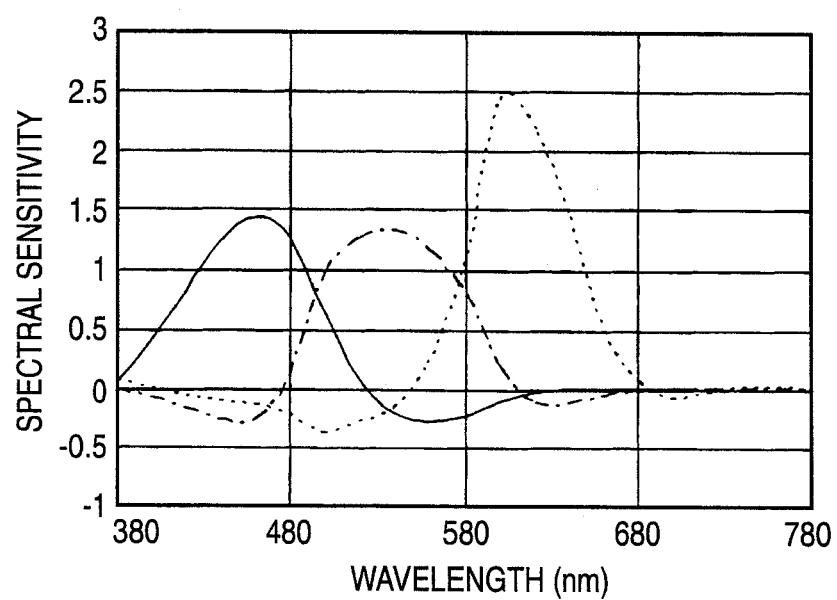
FIG. 18 is a chart showing a characteristic obtained by carrying out a processing of causing a characteristic of each of an R photoelectric converting device, a G photoelectric converting device and a B photoelectric converting device in the imaging device illustrated in FIG. 1 to be close to the characteristic illustrated in FIG. 17.

FIG. 18 is a chart showing the spectral sensitivity characteristics of the R photoelectric converting device, the G photoelectric converting device and the B photoelectric converting device in the imaging device 100 which are obtained as a result of the calculation of the Equations (4) to (6) using the coefficients determined by the method. In FIG. 18, an axis of ordinates indicates a spectral sensitivity obtained with one set to be a reference and an axis of abscissas indicates a wavelength. A curve R shown in FIG. 18 represents a spectral sensitivity characteristic obtained as a result of the approximation of the spectral sensitivity characteristic of the R photoelectric converting device to an ideal spectral sensitivity characteristic, a curve G shown in FIG. 18 represents a spectral sensitivity characteristic obtained as a result of the approximation of the spectral sensitivity characteristic of the G photoelectric converting device to the ideal spectral sensitivity characteristic, and a curve B shown in FIG. 18 represents a spectral sensitivity characteristic obtained as a result of the approximation of the spectral sensitivity characteristic of the B photoelectric converting device to the ideal spectral sensitivity characteristic.

As is apparent from FIG. 18, a sensitivity in an infrared region having a wavelength of 680 nm or more can be set to be almost zero or less. Therefore, it is apparent that the color reproducibility of the color image data can be enhanced by an execution of the calculation processing expressed in the Equation (3).

The display control portion 58 serves to carry out a control for causing the display device 59 to display an image based on the high contrast infrared image data enhanced by the image enhancing portion 57, to carry out a control for causing the display device 59 to display an image based on the high color reproducing color image data, and to carry out a control for causing the display device 59 to display an image obtained by synthesizing the image based on the high contrast infrared image data and the image based on the high color reproducing color image data. Referring to the high contrast infrared image data, a signal level is expressed in a false color and an image is thus displayed or the signal level is converted into an amount of oxygen absorption and an image is thus displayed.

As described above, according to the endoscopic apparatus in accordance with the embodiment, it is possible to generate the high color reproducing color image data having the color reproducibility enhanced more greatly than the color image data and the high contrast infrared image data having the contrast enhanced more greatly than the infrared image data by the calculation processing using the color image data generated from the R signal, the G signal and the B signal which are output from the imaging device 100 and the infrared image data generated from the IRr signal output from the imaging device 100. Therefore, it is possible to enhance precision in an inspection of the endoscopic apparatus more greatly than that in the related art.

By employing the structure described in the first embodiment as the imaging device to be used in the endoscopic apparatus, moreover, it is possible to obtain the high color reproducing color image data and the high contrast infrared image data by one imaging. Consequently, it is possible to carry out an inspection without worrying about a color shift.

According to the endoscopic apparatus in accordance with the embodiment, furthermore, an infrared cut filter is not required. Therefore, a size of a portion to be inserted into a human body can be reduced and a cost of the apparatus can also be reduced.

While the correcting filter 52 is provided in the endoscopic apparatus in the description, it may be omitted. In the case in which the correcting filter 52 is omitted, the spectral sensitivity characteristic of the imaging device 100 to be loaded onto the endoscopic apparatus is obtained as shown in FIG. 6 so that the color reproducibility of the color image data is reduced more greatly. Consequently, the processing carried out by the high color reproducing color image data generating portion 56 can produce advantages more greatly.

While both the high contrast infrared image data generating portion 55 and the high color reproducing color image data generating portion 56 are provided in the endoscopic apparatus in the embodiment, moreover, the high color reproducing color image data generating portion 56 may be omitted. In the case in which the high color reproducing color image data generating portion 56 is omitted, it is preferable to provide the correcting filter 52 for cutting a wave range of 780 nm or more.

Moreover, the high color reproducing color image data generating portion 56 is not restricted to the endoscopic apparatus but is loaded onto an imaging apparatus such as a digital camera for loading an imaging device capable of outputting a signal having an R component, a signal having a G component, a signal having a B component and a signal having an IR component so that the advantages can sufficiently be obtained. In this case, an infrared cut filter is not required for the imaging apparatus. Therefore, it is possible to reduce a size and a cost of the imaging apparatus.

It is possible to implement the function of each of the infrared image data generating portion 53, the color image data generating portion 54, the high contrast infrared image data generating portion 55, the high color reproducing color image data generating portion 56 and the image enhancing portion 57 in the endoscopic apparatus by executing a program for functioning a computer as each of the portions through a computer such as a calculation processing apparatus loaded onto the endoscopic apparatus. Moreover, it is also possible to implement the function by exactly fetching an imaging signal obtained from the imaging device 100 into a personal computer and executing the program through the computer.

In the specification, the wave range of R indicates a range of a wavelength of approximately 550 nm to 700 nm, the wave range of G indicates a range of a wavelength of approximately 450 nm to 610 nm, the wave range of B indicates a range of a wavelength of approximately 380 nm to 520 nm, the infrared region indicates a range of a wavelength of approximately 680 nm to 3000 nm, the wave range of Cy indicates a range of a wavelength of approximately 380 nm to 610 nm, the wave range of Mg indicates ranges of a wavelength of approximately 380 nm to 500 nm and a wavelength of approximately 600 nm to 700 nm, and the wave range of Ye indicates a range of a wavelength of approximately 470 nm to 700 nm.

In the specification, moreover, "transmit a light in a certain wave range" implies that approximately 60% of the light in the wave range or more is transmitted and "absorb a light in a certain wave range" implies that approximately 50% of the light in the wave range or more is absorbed.

According to the invention, it is possible to provide an imaging device capable of obtaining plural kinds of image data (for example, RGB color image data and infrared image data) by one imaging.

The entire disclosure of each and every foreign patent application from which the benefit of foreign priority has been claimed in the present application is incorporated herein by reference, as if fully set forth.

What is claimed is:

1. An endoscopic apparatus comprising:
an imaging device comprising:
a semiconductor substrate;
a plurality of in-substrate photoelectric converting devices arranged on the same plane in the semiconductor substrate;
a plurality of on-substrate photoelectric converting devices, formed on the same plane above the semiconductor substrate, each of which corresponds to each of at least a part of said plurality of in-substrate photoelectric converting devices and comprises a first electrode formed above the semiconductor substrate, a photoelectric converting layer formed on the first electrode and a second electrode formed on the photoelectric converting layer;
a color filter layer that is formed above the semiconductor substrate; and wherein the color filter layer comprises a plurality of color filters corresponding to said plurality of in-substrate photoelectric converting devices respectively, and wherein said plurality of color filters comprise at least three types of color filters that transmit lights in different wave ranges from each other,
said at least three types of color filters transmit a part of a light in a visible region respectively and at least one of said at least three types of color filters also transmits a light in an infrared region, and
the photoelectric converting layer of the on-substrate photoelectric conversion devices absorbs radiation in the infrared region and generates an electric charge corresponding to conversion of the radiation in the infrared region as infrared generated charge, and said photoelectric converting layer of the on-substrate photoelectric conversion devices transmits radiation in the visible light region to the in-substrate photoelectric converting devices through the first electrode, said first electrode being transparent to the visible light region, and said in-substrate photoelectric converting devices generates electric charge corresponding to conversion of the radiation in the visible light region as visible light generated charge;
said imaging device further including a signal reading section configured to read a first signal corresponding to the infrared generated charge and a separate second signal corresponding to the visible light generated charge; and an image data generating section that generates image data corresponding to a time that an inspecting target is visually seen and image data obtained by causing an internal change in the inspecting target to be visible from a signal obtained by imaging through the imaging device.

2. The endoscopic apparatus comprising: the imaging device according to claim 1, wherein said plurality of color filters comprise a color filter that transmits a light in a wave range of R (red), a color filter that transmits a light in a wave range of G (green) and a color filter that transmits a light in a wave range of B (blue).

3. The endoscopic apparatus comprising: the imaging device according to claim 2, wherein the color filter that transmits the light in the wave range of R also transmits radiation in the infrared region, and the part of said plurality of in-substrate photoelectric converting devices correspond to the color filter that transmits the light in the wave range of R.

4. The endoscopic apparatus comprising: the imaging device according to claim 1, wherein said plurality of color filters comprise a color filter that transmits a light in a wave range of Cy (cyan), a color filter that transmits a light in a wave range of G (green) or a light in a wave range of Mg (magenta) and a color filter that transmits a light in a wave range of Ye (yellow).

5. The endoscopic apparatus comprising: the imaging device according to claim 1, wherein said plurality of color filters comprise a color filter that transmits a light in a wave range of Cy (cyan), a color filter that transmits radiation the infrared region, and a color filter that transmits a light in a wave range of Ye (yellow), and the photoelectric converting layer absorbs a light in a wave range of G (green).

6. The endoscopic apparatus comprising: the imaging device according to claim 5, wherein the part of said plurality of in-substrate photoelectric converting devices correspond to the color filter that transmits the light in the wave range of Cy or the color filter that transmits the light in the wave range of Ye.

7. The endoscopic apparatus comprising: the imaging device according to claim 1, wherein the color filter is formed above the on-substrate photoelectric converting device.

8. The endoscopic apparatus comprising: the imaging device according to claim 7, further comprising a protective layer, provided between the on-substrate photoelectric converting device and the color filter layer, that protects the on-substrate photoelectric converting device formed by an atomic layer chemical vapor deposition method, wherein the photoelectric converting layer comprises an organic material.

9. The endoscopic apparatus comprising: the imaging device according to claim 8, wherein the protective layer comprises an inorganic material.

10. The endoscopic apparatus comprising: the imaging device according to claim 9, wherein the protective layer has a two-layer structure that comprises an inorganic layer including an inorganic material and an organic layer including an organic polymer.

11. The endoscopic apparatus comprising: the imaging device according to claim 1, further comprising a microlens, provided above the color filter layer, that collects a light into each of said plurality of in-substrate photoelectric converting devices.

12. The endoscopic apparatus comprising: the imaging device of claim 1, wherein the signal reading section is configured to read the second signal as signal charges from each of the plurality of in-substrate photoelectric converting devices corresponding to respective charges resulting from conversion of respective radiation of respective types of color filters.

13. The endoscopic apparatus comprising: the imaging device of claim 1, wherein an insulator layer is disposed under the first transparent electrode, to electrically separate the on-substrate photoelectric conversion devices from the in-substrate photoelectric conversion device.

14. The endoscopic apparatus comprising: the imaging device of claim 13, wherein the insulator layer is transparent to visible light.

15. The endoscopic apparatus comprising: the imaging device of claim 14, wherein the insulator layer includes an electrical contact region buried therein, said electrical contact region conveying the infrared generated charges for read out as the first signal by the signal reading section.

16. The endoscopic apparatus comprising: the imaging device of claim 14, wherein the insulator layer includes plural electrical contact regions buried therein, said electrical contact regions conveying infrared generated charges from corresponding areas of the photoelectric converting layer, said corresponding areas underlying respectively the three types of color filters, and said plural contact regions convey infrared generated charges generated in the corresponding areas of the photoelectric converting layer for read out as the first signal by the signal reading section.

* * * * *